(12) United States Patent
Nicolaides et al.

(10) Patent No.: US 7,660,686 B1
(45) Date of Patent: Feb. 9, 2010

(54) ION IMPLANT METROLOGY SYSTEM WITH FAULT DETECTION AND IDENTIFICATION

(75) Inventors: Lena Nicolaides, Castro Valley, CA (US); Alexei Salnik, San Jose, CA (US); Bin-ming Benjamin Tsai, Saratoga, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 12/098,991

(22) Filed: Apr. 7, 2008

(51) Int. Cl.
*G01N 37/00* (2006.01)
*G01N 21/00* (2006.01)
(52) U.S. Cl. .................... 702/82; 356/237.1
(58) Field of Classification Search .......... 702/81, 702/82, 182, 185; 356/36, 237.5, 432, 237.1
See application file for complete search history.

(56) References Cited

U.S. PATENT DOCUMENTS

| | | | |
|---|---|---|---|
| 4,634,290 A | 1/1987 | Rosencwaig et al. ........... 374/5 |
| 4,646,088 A | 2/1987 | Inoue .................... 340/870.31 |
| 4,679,946 A | 7/1987 | Rosencwaig et al. ........... 374/5 |
| 4,854,710 A | 8/1989 | Opsal et al. ................. 356/432 |
| 5,074,669 A | 12/1991 | Opsal ........................ 356/445 |
| 5,854,719 A | 12/1998 | Ginosar et al. ................ 360/69 |
| 5,978,074 A | 11/1999 | Opsal et al. .................... 356/72 |
| 6,452,685 B2 | 9/2002 | Opsal et al. ................. 356/601 |
| 6,989,899 B2 | 1/2006 | Salnik et al. ................ 356/432 |
| 7,002,690 B2 | 2/2006 | Salnik et al. ................ 356/432 |
| 2005/0036136 A1* | 2/2005 | Opsal et al. ............. 356/237.2 |
| 2008/0036998 A1* | 2/2008 | Salnik et al. .................. 356/36 |
| 2008/0255786 A1* | 10/2008 | Jin et al. ...................... 702/81 |

* cited by examiner

*Primary Examiner*—Bryan Bui
(74) *Attorney, Agent, or Firm*—Joshua D. Isenberg; JDI Patent

(57) ABSTRACT

Samples subject to ion implantation are measured using a modulated optical reflectance system and the results of the measurements are compared to specification ranges for acceptable samples and a plurality of parametric ranges. Each parametric range is associated with a different known type of implantation fault. Measurement results outside of the specification range may be characterized by fault type by comparing the measurement results to a plurality of parametric ranges. In this way, a fault type may be quickly identified and the corresponding source of the fault may be corrected.

21 Claims, 4 Drawing Sheets

ION IMPLANT METROLOGY SYSTEM WITH FAULT DETECTION AND IDENTIFICATION

TECHNICAL FIELD OF THE INVENTION

The subject invention relates to optical devices used to non-destructively evaluate semiconductor wafers. In particular, the present invention relates to systems for detecting and identifying faults in dopant concentrations in semiconductor samples.

BACKGROUND

As geometries continue to shrink, manufacturers have increasingly turned to optical techniques to perform non-destructive inspection and analysis of semiconductor wafers. In optical metrology the reflected energy that results when an optical beam is directed at a sample can be analyzed using a range of different optical techniques. One known optical metrology technique is Modulated Optical Reflectance (MOR) sometimes also called photo-modulated reflectance (PMR). In this technique a pump laser is switched on and off to create an intensity-modulated pump beam. The pump beam is projected against the surface of a sample causing localized heating of the sample. As the pump laser is modulated, the localized heating (and subsequent cooling) creates a train of thermal and plasma waves which reflect and scatter off various features and interact with various regions within the sample to alter the flow of heat and/or plasma from the pump beam spot. These thermal and plasma waves have a direct effect on the surface reflectivity of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be investigated.

PhotoModulated Reflectance (PMR) type systems use external means to induce thermal or plasma waves in the sample under study. PMR-type systems, used to study a range of attributes including material composition and layer thickness, are described in more detail in U.S. Pat. Nos. 4,634,290; 4,646,088; 4,679,946; 4,854,710; 5,854,719; 5,978,074; 5,074,669; and 6,452,685, each of which is incorporated by reference herein.

PMR-type systems can be used for the measurement and analysis of the dopants added to semiconductor wafers. Dopants are ions that are implanted to semiconductors during a process known as ion implantation. Ion implantation damages the crystal lattice as incoming ions come to rest. This damage is typically proportional to the concentration and depth of ions within the crystal lattice. This makes measurement of damage an effective substitute for direct measurement of dopant concentration and depth. PMR-type systems have proven to be adept at measuring damage and have been widely used for post implantation evaluation.

The relationship between dopant concentration and the PMR amplitude is monotonic for low dopant concentrations. As dopant concentration increases the monotonic relationship breaks down. At high concentrations, the PMR amplitude behavior sometimes is no longer monotonic and as a result cannot be used to accurately derive corresponding dopant concentrations. The same sort of breakdown may occur as implanted ions become heavier (e.g., $As^+$ or $P^+$ ions). In both cases, this is attributable to the formation of a Si amorphous layer resulting in modulated interference effects. PMR phase information becomes flat or insensitive to changes in concentration at high dopant concentrations or where heavy ions are implanted.

Measuring the DC reflectivity of both the pump and probe beams in addition to the modulated optical reflectivity signal carried on the probe beam, i.e., using the DC reflectivity data at two wavelengths often resolves some ambiguities in the measurement caused, for example by the presence of the Si oxide layer on the surface of the sample. See U.S. Pat. No. 5,074,669 (incorporated in this document by reference).

A method to provide this type of reliable and effective measurement capability for high dopant concentrations and ion implantation of relatively heavy ions is shown in U.S. Pat. Nos. 6,989,899 and 7,002,690, both of which have been incorporated herein by reference.

This prior art method simultaneously monitors ion implantation dose, damage and/or dopant depth profiles in ion-implanted semiconductors. The measurement method is logically divided into two steps: a calibration and a measurement step. During the calibration step, the photo-modulated reflectance of a known damage profile is characterized, using a PMR-type optical metrology tool to record both quadrature (Q) and in-phase (I) values for a series of specially prepared calibration subjects. Each calibration subject is fabricated at the same implantation energy. As a result, variations recorded by the system are largely attributable to variations in dopant concentration.

In the measurement step, I-Q measurements for a test subject are obtained empirically. A calibration line is defined within an I-Q plane. The slope of the calibration line is defined by the implantation energy used to create the calibration subject. The calibration line is used to define a calibration region within the I-Q plane, by defining an upper boundary line that has a slightly greater slope than the calibration line and a lower boundary line that has a slightly smaller slope than the calibration line. The calibration region is the area between the upper and lower boundary lines and includes all points within a specified distance (often defined in terms of a percentage) of the calibration line. For each subject wafer, the PMR-type system makes one or more measurements. Measurements that fall within the calibration region are known to have the damage profile close to that of the calibration subject.

The empirically obtained I-Q measurements are then compared to determine if they fall within the identified calibration region of I-Q space. This comparison indicates whether the test subject has a damage profile that is similar to the known damage profile. Measurements that do not fall within this region are assumed to deviate from the known damage profile of the calibration subject. Details of the method are set forth in the aforementioned U.S. Pat. Nos. 6,989,899 and 7,002,690.

While MOR can provide an effective method of accepting or rejecting wafers that provide acceptable accuracy even when dopant concentrations are high or where heavy ions have been implanted, it does not attempt to address the nature and character of those measurements which fall outside of the calibration region.

Prior art systems for ion implant metrology such as MOR are capable of detecting faults by measuring the MOR signal magnitude at a given time interval. However, no identification of faults have been performed on the system itself, leaving it up to the operator to determine off-line what kind of implanter malfunction caused each particular fault. In addition, prior art systems use only the MOR signal to monitor implanters for potential faults. Therefore prior art systems are unable to identify the cause of faults of certain types, e.g., faults caused by the wrong energy, the wrong dose, the wrong species, etc.

It is within this context that embodiments of the present invention arise.

BRIEF DESCRIPTION OF THE DRAWINGS

Other objects and advantages of the invention will become apparent upon reading the following detailed description and upon reference to the accompanying drawings in which.

DETAILED DESCRIPTION OF THE PREFERRED EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Certain embodiments of the current invention relate to using Modulated Optical Reflectance (MOR) measurement technique for ion implant metrology. The MOR technique utilizes an intensity modulated pump laser beam to create carrier plasma and thermal waves in a semiconductor sample. A second probe laser beam reflects from the excited area and the changes in optical reflectance coefficient caused by the propagating plasma and thermal waves are recorded as the MOR signal. Commercial systems utilizing the MOR technology (Therma-Probe) are being used primarily for daily monitoring of wafers coming out of implantation systems. Any deviations from the specified range of MOR signal variations indicate malfunctions (or faults) of the implanter of one of several types. Additionally, Q and I components of the MOR signal can be analyzed in a Q-I space in the way described in the U.S. Pat. Nos. 6,989,899 and 7,002,690 assigned to the assignee of the present invention and incorporated herein by reference. Thus the precise identification of implanter fault cause may be obtained.

Figure 1:
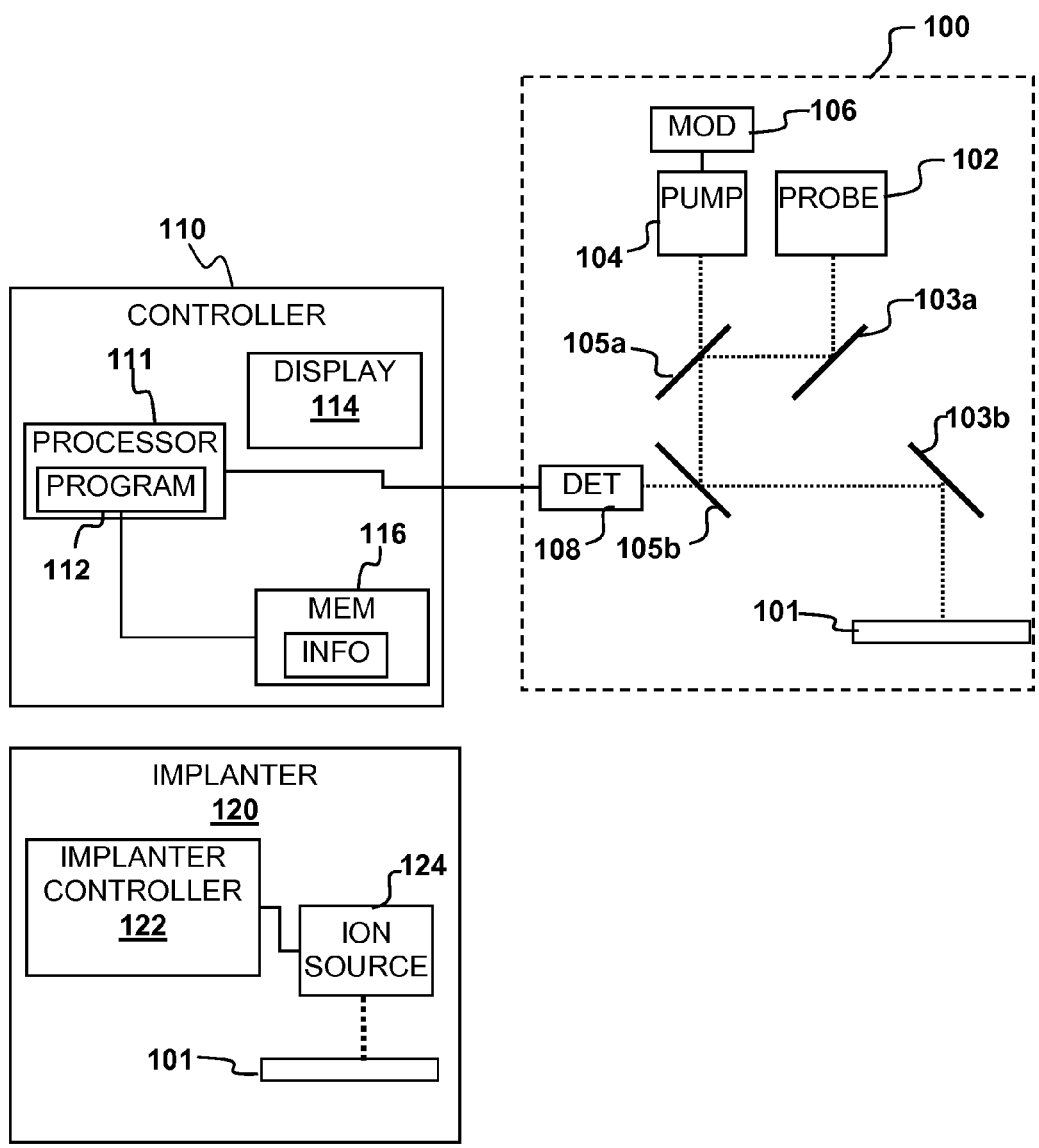
FIG. 1 is a schematic representation of a system and method for detecting and identifying faults in accordance with an embodiment of the present invention.

As seen in FIG. 1, a system 99 in accordance with an embodiment of the invention may include a metrology tool 100, a system controller 110 and an implanter 120. The metrology tool 100 performs measurements on samples, e.g., semiconductor substrates that have been processed by the implanter 120, which implants ions from an ion source 124 into samples 101. The system controller includes a processor 111 running a program 112 that analyzes the results of the measurements performed with the metrology tool 100. A sample 101 can be monitored throughout its progress through the implanter 120 during the implant process by the controller 110. A program 112 running on the controller enables an operator to identify and characterize implant faults and make adjustments to the implant process to sharply reduce or eliminate such faults. Preferably the computer program 112 may provide feedback to an implanter/controller 122 to enable the implanter/controller 122 to automatically adjust the implant process carried out by the implanter 120 to eliminate the fault without the intervention of the operator. The measurement system 100 may also provide input to the implanter/controller 122 to control the implant process and minimize faults occurring during the process, e.g., by controlling the energy and/or dose of ions delivered to subsequent samples 101 by the ion source.

By way of example, the metrology tool 100 may be a modulated optical reflectance (MOR) tool. During MOR measurement with the tool 100, a probe beam from a probe laser 102 is directed at the portion of a sample 101 via mirrors 103a, 103b and beam splitters 105a, 105b. The same portion of the sample 101 is simultaneously illuminated by a modulated pump beam from a pump laser 104. A modulator 106 coupled to the pump laser 104 provides modulation to the pump beam. A portion of the probe beam is reflected back to a photodetector 108 via mirror 103b and beamsplitter 105b. The photodetector 108 converts the intensity of the reflected probe beam to an electrical signal that is coupled to a processor 111. The processor filters the output signal from the photodetector 108 to isolate the changes that are synchronous with the pump beam modulation (See U.S. Pat. No. 5,978,074). Separate "in-phase" (I) and "quadrature" (Q) outputs are then used to calculate amplitude and phase of the modulated signal:

$$\text{Amplitude} = \sqrt{(I^2 + Q^2)} \qquad (1)$$

$$\text{Phase} = \arctan\left(\frac{Q}{I}\right) \qquad (2)$$

The program 112 may use the amplitude and phase values to deduce physical characteristics of the sample for one or more specially prepared calibration samples, each of which has known physical characteristics. The empirically derived values may be stored and later used to associate known physical characteristics with corresponding amplitude values and phase values. Amplitude and phase values obtained for production samples that have been processed by the implanter 120 can then be analyzed by comparison to the amplitude and phase values obtained for the calibration samples.

According to an embodiment of the present invention, Quadrature (Q) and In-Phase (I) components of an MOR signal may be recorded in the course of the implanter monitoring. Samples 101 that have been processed by the implanter 120 may be measured by the optical metrology system 110 (e.g., an MOR system). An MOR amplitude constructed from the recorded Q and I components of the MOR signal may also be tracked during the course of the monitoring. Once a deviation from the average MOR signal amplitude is recorded exceeding predetermined values, i.e., specifications, the MOR amplitude is analyzed by a corresponding software program to determine if the magnitude of this deviation falls within one or more predetermined ranges each of which corresponds to an implanter fault of a certain type.

In particular, during a calibration phase the photo-modulated reflectance of a calibration sample having a known damage profile may be measured and characterized as corresponding to a particular region in I-Q space. The known damage profile may correspond to a known fault type. This process may be repeated for different calibration samples having different damage profiles corresponding to different fault types. In a subsequent measurement step, the photo-modulated reflectance of a production sample 101 may be empirically measured to obtain in-phase and quadrature values. The in-phase and quadrature values are then compared, in I-Q space, to the regions of I-Q space corresponding to damage profiles for known fault types to identify and characterize any faults in the implantation of the sample 101. The program 112 may display the fault type and/or damage profile information derived from amplitude and phase measurements on a display 114 or store the fault type and/or damage profile information in a memory 116 so that the operator can perceive or retrieve the information and take appropriate action in response to it.

The program 112 may also be configured to provide feedback to an implanter controller 122 that controls the implanter 120. In particular, the program may provide fault type and damage profile information derived from amplitude and phase measurements. The implanter controller 122 may use this information to adjust the ion implantation process taking place in the implanter 120 for subsequent samples. For example, variations in implanter beam current can be detected by the optical metrology system (e.g., an MOR system) and controller 122 can use this information to adjust the beam current in implanter.

Figure 2:
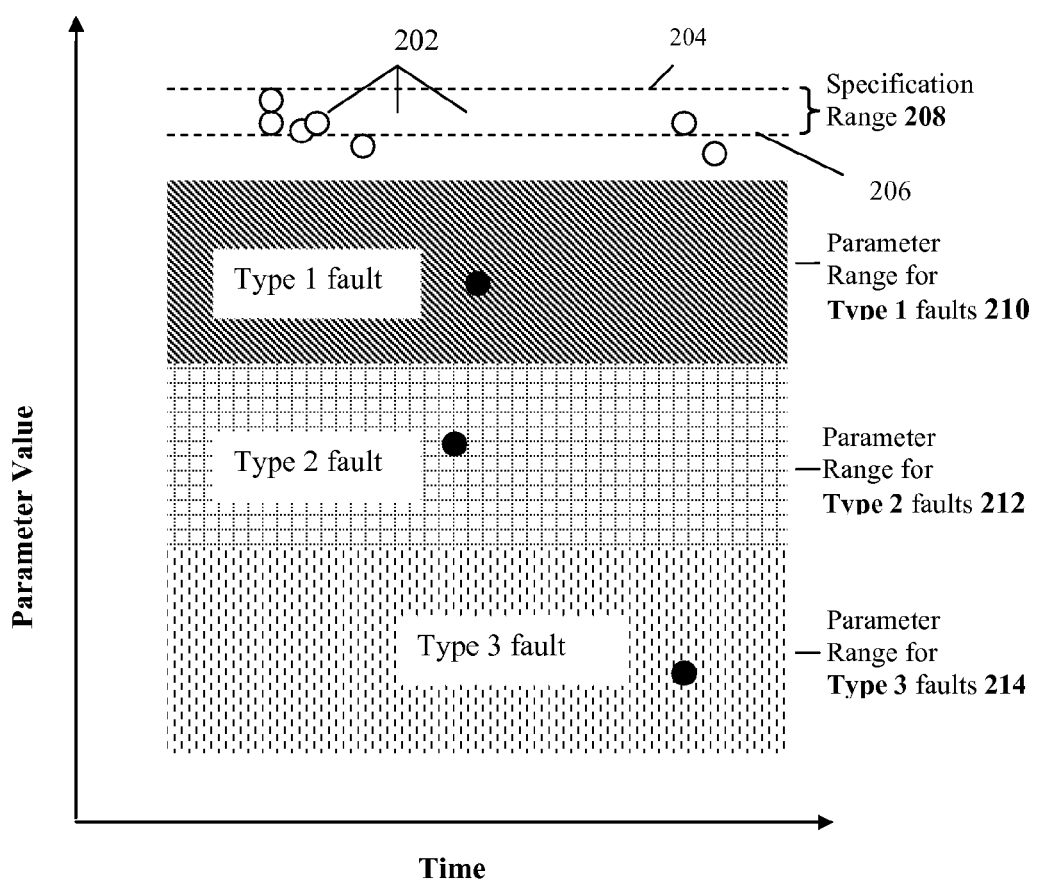
FIG. 2 is a plot of monitoring parameters versus time, showing parameter deviation ranges for different types of faults in accordance with an embodiment of the present invention.

The computer program 112 may be configured to analyze Q-I data to compare data points derived from a sample 101 with designated parameter ranges. By way of example, as shown in FIG. 2, the monitoring parameters may be plotted against time and show a series of parameter ranges, each range denoting a particular type of ion implantation fault associated with that range. As seen in FIG. 2, the majority of data points, designated by circles 202, are found between an upper limit 204 and a lower limit 206 of a specification range 208. The specification range 208 sets the upper and lower limits for acceptable ion implantation parameters observed during processing.

A parameter range 210 defines upper and lower limits for Type 1 faults. Parameter range 212 defines the upper and lower limits for Type 2 faults. Parameter range 214 defines the upper and lower limits for Type 3 faults. The correlation between fault types and the parameter ranges may be done empirically. Ranges for each fault type may be determined by calibrating the system for generating known faults in a statistically significant number of sample wafers and measuring the parameters, e.g., Q and I signals for each fault type.

The program 112 may be configured to monitor a predetermined parameter best suited for detection of processing system faults. For example, when a deviation from the lower limit 206 is detected, the software program 112 may use the magnitude of this deviation to identify the cause of a particular fault. In FIG. 2, faults of different types have different ranges of deviation magnitudes (parameter ranges). By selecting predetermined ranges of deviation, a type of fault (Type 1-3 faults) can be determined from the comparison of the experimental deviation and the predetermined deviation. The three different ranges 210, 212, 214 corresponding to three different types of faults are shown schematically in FIG. 2. However, the concept may be extended to any number of distinct types of faults.

For overlapping parameter ranges, a metrology signal different from MOR amplitude (MOR phase, DC reflectances, etc.) may be used to identify the fault. Alternatively, the Q-I analysis described below may be used in this case.

Figure 3:
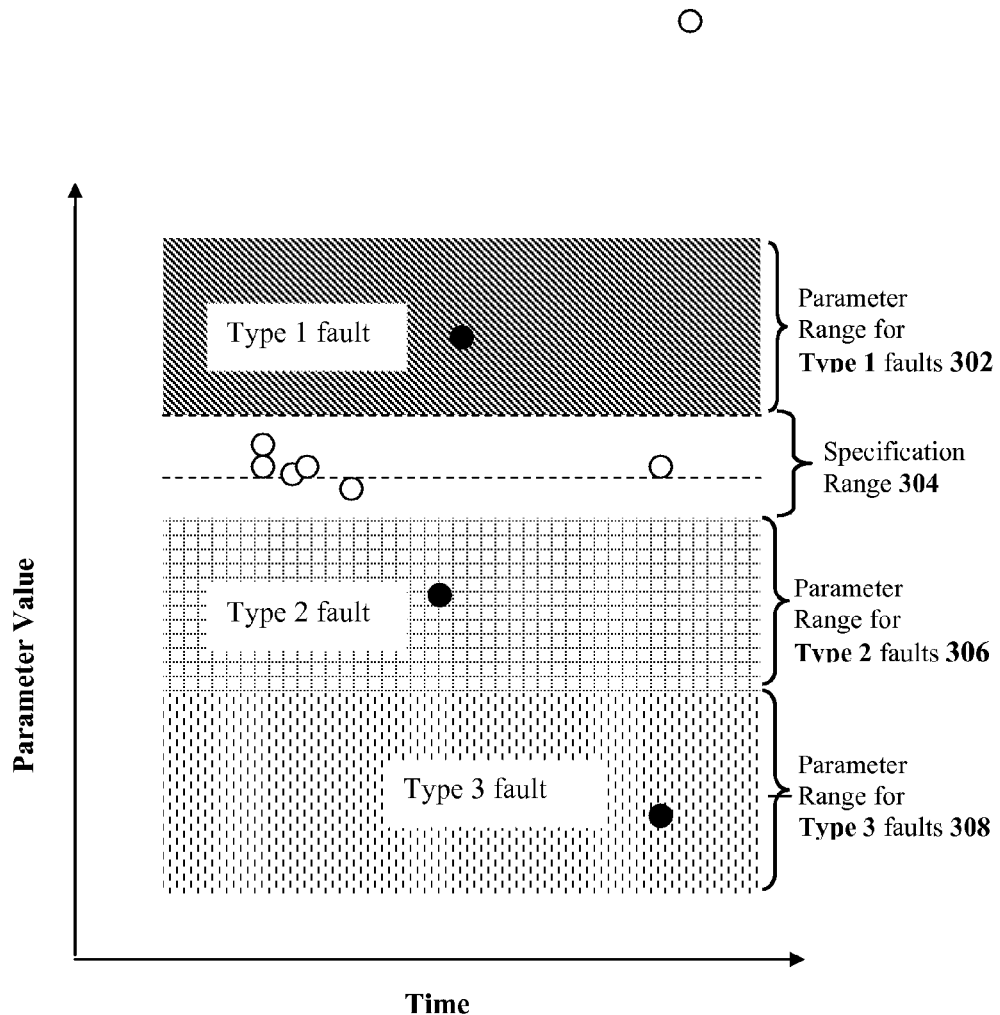
FIG. 3 is a plot similar to FIG. 2, in which one deviation range has an opposite sign when compared to other ranges.

FIG. 3 shows another example of a plot similar to the plot of FIG. 2. However, in FIG. 3, the parameter range 302 for Type 1 faults is above the specification range 304, i.e., the parameter range 302 for Type 1 faults has an opposite sign compared to parameter ranges 306 and 308, for Type 2 and Type 3 faults, respectively.

Figure 4:
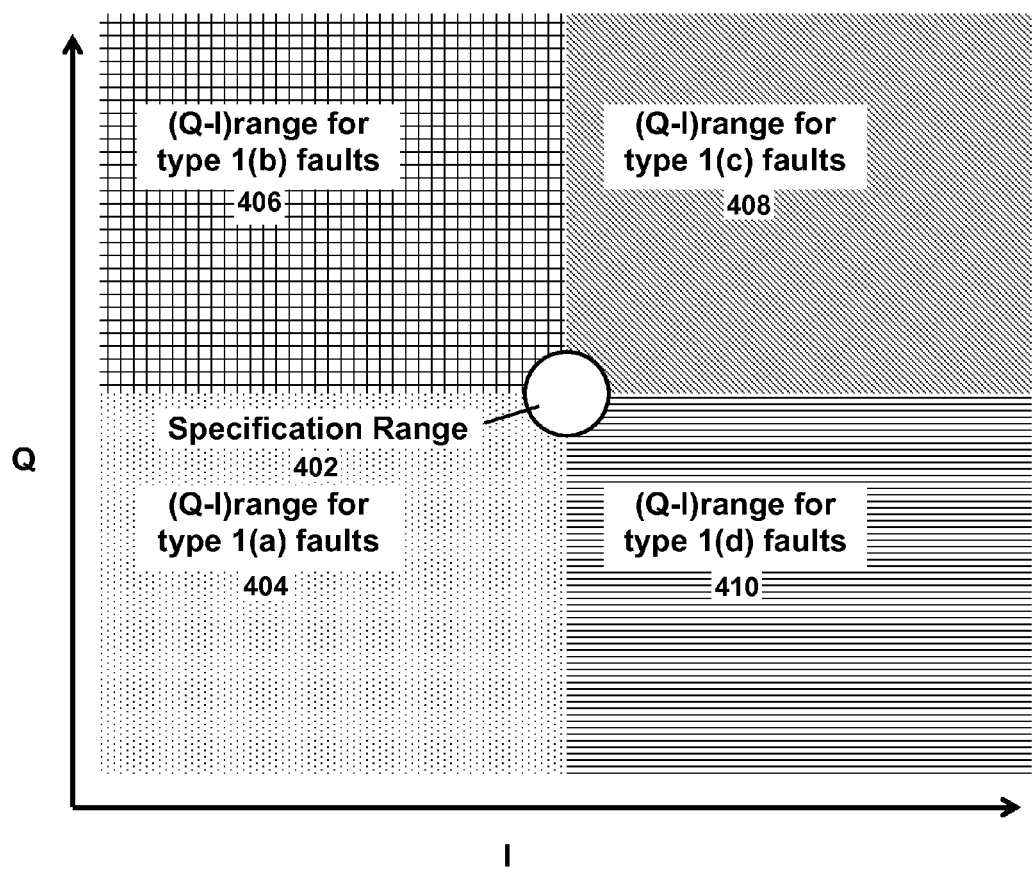
FIG. 4 is a plot of faults events analyzed in Q-I space in accordance with an embodiment of the present invention.

An analysis of fault events in Q-I space is shown schematically in FIG. 4. In this figure, a predetermined specification range 402 of Q-I variations is shown in the center surrounded by four possible deviation ranges or quadrants in a Q-I plot. In FIG. 4, Q-I range 404, the lower left-hand quadrant, represents the parametric range for Type 1(a) faults. Q-I range 406, the upper left-hand quadrant, represents the parametric range for Type 1(b) faults. Q-I range 408, the upper right-hand quadrant, represents the parametric range for Type 1(c) faults. Q-I range 410, the lower right-hand quadrant, represents the parametric range for Type 1(d) faults. It is noted that each of the Q-I parametric ranges within each quadrant may be further subdivided to identify particular fault types.

Implanter faults may occur at different stages of the semiconductor fabrication process: pre-implant, implant and dopant activation (anneal). As an example, Table 1 below shows a list of potential fault types and their characteristic causes.

TABLE 1

| Monitoring | Fault Type | Causes |
| --- | --- | --- |
| Pre-Implant | 1) Screen Oxide/Nitride thickness error<br>2) Photoresist stripping error<br>3) Mask Error | Diffusion,<br>Photolithography,<br>Inventory error |
| Implant | 1) No Implant<br>2) Double Implant<br>3) Backside Implant<br>4) Two-step implants | Operator error,<br>Implanter<br>malfunction |
|  | 1) Dose/Energy/Species selection error<br>2) Scan set-up error | Operator set-up errors |
|  | 1) Partial or intermittent implant<br>2) Beam current error<br>3) Dosimetry internal circuitry faults<br>4) Leakage current<br>5) Capacitively coupled noise errors<br>6) Broken wafer fragment errors<br>7) Scan lock-up(transient or steady state)<br>8) Vacuum loss errors<br>9) Ion energy errors<br>10) Ion beam contamination<br>11) Wafer charging dose errors<br>12) Tilt angle set-up | Implanter<br>malfunction |
| Anneal | 1) Activation<br>2) Anneal errors | Implant,<br>Diffusion errors |

In the event of wrong dose, energy, and species, the Q-I analysis described above allows an implanter operator to decouple faults caused by these three malfunctions. Therefore, more precise identification of faults may be performed.

Embodiments of the present invention allow a user to perform advanced fault detection and identification in real time without operator intervention, thus reducing the cost and increasing the throughput of the semiconductor fabrication process. It also allows correcting the manufacturing process for errors in a more efficient and timely fashion.

As described above, instead of the MOR amplitude and Q-I values, other MOR or any combination of the MOR measurement parameters may be used for monitoring potential faults. In another embodiment, fault detection and identification may be used on maps of unprocessed and processed wafers and this procedure may be also monitored over predetermined time periods.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A" or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for identifying and characterizing faults occurring during ion implantation of a sample, the method comprising:

establishing a specification range for a value of a modulated optical reflectance (MOR) parameter characteristic of ion implantation in acceptable processed samples;

establishing multiple parametric ranges for the parameter outside of the specification range wherein each parametric range is associated with a different fault occurring during ion implantation of a processed sample;

measuring a value of the parameter for the sample with an optical metrology reflectance system using a modulated optical reflectance technique;

determining if the value of the parameter is outside the specification range; and if the value of the parameter is outside the specification range, determining whether the value of the parameter lies within one of the parametric ranges, and storing or displaying identifying the corresponding fault in a manner retrievable or perceptible by a user.

2. The method of claim 1 wherein the specification range and each parametric range is defined in terms of one or more quantities derived from a modulated optical reflectance signal.

3. The method of claim 2 wherein the specification range and each parametric range includes optical Quadrature (Q) component and an In-Phase (I) component of a Modulated Optical Reflectance signal.

4. The method of claim 1, wherein the specification range and the parametric ranges represent a continuous spectrum extending above and below the specification range, with the specification range defined by upper and lower limits, and each parametric range defined by bracketing distinct ranges of values extending across such spectrum and outside the specification range.

5. The method of claim 4, wherein faults are characterized as Type 1 faults, Type 2 faults or Type 3 faults, depending on the parametric range in which the parameter value falls.

6. The method of claim 5, further comprising enabling adjustment of the ion implantation process to eliminate such type of fault in subsequent processing.

7. A method for identifying and characterizing faults occurring during ion implantation of a sample, the method comprising:

establishing a specification range for a parameter occurring in acceptable processed samples within a continuum for Quadrature (Q) and In-Phase (I) modulated optical reflectance output values occurring during ion implantation;

establishing multiple parametric ranges outside of the specification range for faults occurring during the processing of a sample;

measuring a value of the parameter for a sample by a modulated optical reflectance technique with an optical metrology reflectance system;

determining whether or not the value falls within the specification range;

determining if the parameter value falls outside the acceptable specification range; and characterizing a fault associated with the parameter value as to type by determining which of the multiple parametric ranges within which the value falls, wherein each different parametric range of the multiple parametric ranges is associated with a different known type of fault.

8. The method of claim 7, wherein the specification range is defined as a limited region within a continuum of Q-I values and the parametric ranges represent quadrants defining regions of Q-I values adjacent the specification range.

9. The method of claim 8 wherein establishing multiple parametric ranges includes associating a fault type with a parametric range depending on a quadrant within the continuum of Q-I values in which the parametric range falls.

10. The method of claim 9, further comprising enabling adjustment of an ion implantation process to eliminate the type of fault associated with the parameter value in subsequent processing.

11. A system for identifying and characterizing faults occurring during the ion implantation of samples, the system comprising:

an optical reflectance metrology tool configured to measure a value of a parameter characteristic of ion implantation in a sample;

a controller coupled to the metrology tool, said controller being configured to determine whether the value of the parameter is outside a specification range for the parameter wherein the specification range sets the upper and lower limits for acceptable ion implantation parameters observed during processing; and, if the value of the parameter is outside the specification range, determine whether the value of the parameter lies within one of a plurality of predetermined parametric ranges, wherein each predetermined parametric range is associated with a different type of fault occurring during ion implantation of a processed sample and store or display information identifying a fault type corresponding to the parametric range in a manner retrievable or perceptible by a user.

12. The system of claim 11 wherein the controller is further configured to establish the specification range.

13. The system of claim 12 wherein the controller is further configured to establish the plurality of predetermined parametric ranges.

14. The system of claim 13, wherein the specification range and the parametric ranges established by said apparatus represent a continuous spectrum, with the specification range defined by upper and lower limits, and each parametric range defined by bracketing distinct ranges of values extending across such spectrum and outside the specification range.

15. The system of claim 14, wherein faults are characterized by said apparatus as Type 1 faults, Type 2 faults or Type 3 faults, depending on the parametric range in which the fault falls.

16. The system of claim 15, wherein the controller is configured to adjust an ion implantation process in an implanter in response to an identified fault type to eliminate such type of faults in subsequent processing.

17. The system of claim 16, further comprising an implanter responsive to the controller, so that the system is configured to perform advanced fault detection and identification in real time without operator intervention.

18. The system of claim 11, wherein the metrology tool is a modulated optical reflectance (MOR) tool.

19. The system of claim 18 wherein the specification range includes a portion of a continuum for Quadrature (Q) and In-Phase (I) output values from the MOR tool for acceptable processed samples that have undergone ion implantation.

20. The system of claim 19, wherein the specification range is a limited region within a continuum of Q-I values and the parametric ranges represent portions of quadrants defining one or more regions of Q-I values outside the specification range.

21. The system of claim 20 wherein controller is configured to characterize the fault types associated with a parametric ranges differently depending on the quadrant in which the a parametric range falls.

* * * * *